United States Patent [19]

Ferlauto, Jr. et al.

[11] Patent Number: 4,774,077

[45] Date of Patent: * Sep. 27, 1988

[54] STABLE ANTIPLAQUE DENTIFRICE

[75] Inventors: Robert J. Ferlauto, Jr., Edison; Kathleen M. Yuhasz, Fords, both of N.J.

[73] Assignee: Colgate-Palmolive Company, New York, N.Y.

[*] Notice: The portion of the term of this patent subsequent to Dec. 32, 2003 has been disclaimed.

[21] Appl. No.: 75,159

[22] Filed: Oct. 1, 1987

Related U.S. Application Data

[62] Division of Ser. No. 855,993, Apr. 25, 1986, Pat. No. 4,701,318, which is a division of Ser. No. 648,926, Sep. 10, 1985, abandoned.

[51] Int. Cl.$^4$ .......................... A61K 7/16; A61K 7/18; A61K 7/22; B01J 13/00
[52] U.S. Cl. .................................. 424/52; 252/315.3; 252/315.4; 424/54; 514/835
[58] Field of Search ........................ 252/315.3, 315.4; 424/52, 54; 514/835

[56] References Cited

U.S. PATENT DOCUMENTS

| | | | |
|---|---|---|---|
| 3,034,967 | 5/1962 | Apperson et al. | 424/52 |
| 3,124,512 | 3/1964 | Schmid et al. | 424/52 |
| 3,728,446 | 4/1973 | Roberts et al. | 424/54 X |
| 3,842,168 | 10/1974 | Colodney | 424/52 |
| 3,980,767 | 9/1976 | Chown et al. | 424/52 |
| 4,118,476 | 10/1978 | Gaffar et al. | 424/54 |
| 4,130,637 | 12/1978 | Bauman | 424/52 X |
| 4,363,795 | 12/1982 | Wåhlstam | 424/54 |
| 4,490,353 | 12/1984 | Crawford et al. | 424/52 |
| 4,632,825 | 12/1986 | Ferlauto, Jr. et al. | 424/52 |

Primary Examiner—Richard D. Lovering
Attorney, Agent, or Firm—Robert L. Stone; Murray M. Grill

[57] ABSTRACT

A chemically and physically stable antiplaque dentifrice comprising an antiplaque quaternary ammonium compound, a betaine surfactant, a humectant system of glycerin and/or sorbitol and a nonionic gelling agent, prepared by a process which comprises the preparation of two separate gel phases, an oil gel phase and a water gel phase, combining said gel phases into a single gel, and adding a dental abrasive thereto as the final step, or adding said abrasive to the water gel phase prior to the addition of the oil gel phase.

13 Claims, No Drawings

STABLE ANTIPLAQUE DENTIFRICE

This is a Division of Ser. No. 885,993 filed Apr. 25, 1986 which issued Oct. 20, 1987, as U.S. Pat. No. 4,701,318 which is a division of parent Ser. No. 648,926 filed Sept. 10, 1985, now abandoned.

BACKGROUND AND PRIOR ART

The present invention relates to the formulation of an antiplaque dentifrice with improved foaming, improved taste, solubilized active ingredient, improved fluoride stability, improved compatibility of all components, improved extrusion characteristics from various containers and increased cost effectiveness.

Until now it had been difficult to formulate a cosmetically acceptable antiplaque dentifrice consisting of a quaternary ammonium compound and a betaine surfactant with a humectant system of all glycerin or all sorbitol. In addition, the use of mixtures of glycerin/polyethylene glycol or sorbitol/polyethylene glycol, where glycerin or sorbitol were present in excess of 10% by weight of the formulation, displayed marginal cosmetic stability. However, after extensive solubility tests on various mixtures of the components in the benzethonium chloride (BTC) dentifrice, a compatible system of water, BTC, betaine, salts and glycerin was found which was dependent upon the order of addition of these components.

Accordingly, it has been found that by using a specific process, stable formulations of an antiplaque dentifrice containing a quaternary ammonium compound and a betaine surfactant can be made with glycerin or sorbital as the humectant. The essential features in this process is the formation of two separate phases with the subsequent combination of these two phases to form the stable system. One of these phases contains the active quaternary ingredient (benzethonium chloride or cetyl pyridinium chloride) solubilized in the betaine surfactant (cocamidopropyl betaine) and a flavor, which is designated the oil gel phase. The second phase contains water, humectant, and nonionic gelling agent e.g. hydroxyethylcellulose, and optionally sodium saccharin and fluorine-containing compound i.e. sodium monofluorophosphate, and is designated the water gel phase. The dental polishing agent may be added to the combined phases as a final step, or be added to the water gel phase prior to combining with the oil gel phase. The finished product was improved chemical and cosmetic stability and improved taste.

A conventional method of preparing antibacterial dentifrices containing a quaternary ammonium compound as the active material is disclosed in U.S. Pat. No. 4,118,476 and U.S. Pat. No. 4,188,372, and comprises the formation of a gel with humectant (glycerin, sorbitol, polyethylene glycol), thickener (hydroxyethylcellulose), and sweetener, and adding thereto polishing agent, flavor, antibacterial agent, additional water, and lastly an antistain agent (a phosphono-containing compound or a mellitic acid-containing compound).

The prior art also discloses processes for stabilizing a dentifrice against precipitation and flocculation due to the incompatibility of an antibacterial agent and an alkali metal carboxyalkyl cellulose, as shown in U.S. Pat. No. 3,842,168 and No. 3,843,779. The former patent utilizes the steps of adding the antibacterial agent dissolved in water to a non-aqueous blend of the carboxymethylcellulose, sodium saccharin and humectant and then adding the surfactant to form a gel, to which is added the polishing material and flavor as a final step. The latter patent adds the antibacterial agent separately or cojointly with the surfactant to a mixture of glycerin, water, sodium saccharin, carboxymethylcellulose and surfactant, followed by the addition of a polishing material and flavor. The addition of the surfactant must precede or be simultaneous with the antibacterial addition in order to avoid precipitation in the dentifrice.

However, the prior art does not disclose a cosmetic, and chemically stable antiplaque dentifrice containing as the essential ingredients, a quaternary ammonium antiplaque compound, a zwitterionic betaine surfactant, a glycerin and/or sorbitol humectant, and a nonionic gelling agent prepared by a novel process utilizing a specific sequence of steps, which comprises the formation of two separate gel phases, an oil gel phase consisting of the quaternary ammonium compound, betaine surfactant and flavor; and a water gel phase consisting of water, humectant and gelling agent; combining the two gel phases into a single parent gel, and adding a dental abrasive to the combined gel phase as a final step or to the water gel phase prior to the addition of the oil gel phase.

SUMMARY OF THE INVENTION

It has now been found that stable formulations of an anti-plaque dentifrice containing a quaternary ammonium compound, and a betaine surfactant, can be made with glycerin or sorbitol as the humectant by utilizing a specific sequence of steps which comprises the formation of a separate oil gel phase of the quaternary ammonium compound, betaine and flavor, a separate water gel phase of humectant, nonionic gelling agent and water (which may preferably contain the salts, i.e. sodium saccharin and sodium monofluorophosphate or other fluoride salt), combining the oil and water gel phases to form a stable parent gel phase, and adding a dental abrasive as the final step. This process may be varied by adding the polishing agent to the water gel and then adding the oil gel to the water gel-abrasive mixture. This dentifrice is prepared at ambient temperature, i.e. each step in the total sequence of steps is performed at ambient (room) temperature.

Accordingly, a primary object of the present invention is to formulate a stable antiplaque dentifrice based on quaternary active ingredients, and a bentaine surfactant, with improved compatibility of all components, by the formation of two separate gel phases, which are combined to form a stable total gel system.

Another object of the present invention is to provide a cosmetically and chemically stable antiplaque dentifrice containing glycerin and/or sorbitol as humectant which is compatible with the betaine and the quaternary active ingredients.

Still another object of this invention is to provide a stable antiplaque dentifrice containing a nonionic gum, such as hydroxyethylcellulose, as gelling agent to stabilize the betainequat system and to prevent deactivation of the quaternary active ingredient.

Another object of this invention is to provide a cosmetic (physical) and chemically stable antiplaque dentifrice also containing a fluoride-providing compound, without adversely affecting cosmetic stability of the dentifrice.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel stable antiplaque dentifrice of this invention comprising a quaternary ammonium antiplaque compound, a zwitterionic betaine surfactant, flavor, and a humectant selected from the group consisting of glycerin, sorbitol and mixtures thereof, and a nonionic gelling agent is prepared at ambient temperature by the process which comprises the formation of two separate gel phases, an oil gel phase consisting of the quaternary ammonium antiplaque compound, the betaine and a flavor; and a water gel phase consisting of water, humectant and nonionic gelling agent; combining the two gel phases to form a single gel phase; adding a dental abrasive to said combined gel phase. The sequence of addition may be varied by adding the dental abrasive to the water gel phase prior to combining with the oil gel phase. However, it is essential that two separate gel phases be prepared prior to the addition steps. The addition of salts such as fluorine-containing compound and/or sodium saccharin, which are preferred components, is made by dissolving in the formula amount of water prior to mixing the water with the humectant and gelling agent in the formation of the water gel phase.

More specifically, present invention relates to a novel process of preparing a cosmetic and chemically stable antiplaque dentifrice consisting essentially of the formation of two phases, an oil gel phase and a water gel phase comprising the following sequence of steps:

a. dispersing the formula amount of a quaternary ammonium antiplaque agent in the formula amount of flavor, b. mixing said quaternary ammonium-flavor dispersion into the formula amount of betaine surfactant to form the oil gel phase, c. dispersing the formula amount of nonionic gelling agent in the formula amount of glycerin and/or sorbitol humectant, d. mixing said gelling agent-humectant dispersion with the formula amount of water to form the water gel phase, e. combining the two gel phases to form a stable parent gel phase, f. adding the dental abrasive to the water gel phase or to the parent gel phase with mixing, and g. recovering a stable antiplaque dentifrice.

The oil gel phase is in the form of a viscous, translucent gel. The water gel phase is transparent. The stable parent gel phase resembles an emulsified system.

This process may be modified by adding and mixing the dental abrasive with the water gel phase, and then adding the oil gel phase to the mixture of dental abrasive and water gel phase.

Sodium saccharin and/or a fluorine-containing compound, which are optionally preferred additives, are dissolved in the formula amount of water prior to its addition to the humectant-gelling agent dispersion and the formation of the water gel phase.

The new formulation method of instant invention using only glycerin and/or sorbitol humectant in a quaternary-betaine system provides chemical and cosmetic stability to the dentifrice as well as improved taste. The taste characteristics of a 20 % containing-glycerin or sorbitol humectant, benzethonium chloride (BTC), betaine dentifrice are greatly improved when compared to a 20% polyethylene glycol (PEG 600) BTC dentifrice. The stability afforded by the glycerin and/or sorbitol humectant does not extend to other humectants such as polyethylene glycol. A precipitate has been observed in the 20% PEG 600 humectant gel phase of the BTC dentifrice. The precipitate was analyzed using an I.R. spectrophotometric method and was found to be comprised of BTC, saccharin and betaine.

Fluoride stability studies on the BTC dentifrice have confirmed that a large part of MFP loss is due to hydrolysis in an all PEG 600 humectant system. Other phenomena (i.e. adsorption or insolubilization) may be responsible as well. A solubility problem with PEG 600 and monofluorophosphate (MFP) has been found. Stability studies of MFP in the BTC dentifrice indicate that hydrolysis of MFP occurs to a large extent in an all PEG 600 humectant system. However, an all glycerin humectant system in the BTC dentifrice displays much less loss of MFP. In fact an all glycerin humectant system meets the present requirement for MFP shelf life (more than 600 ppm total soluble fluoride, half of which is MFP) while an all PEG 600 humectant system does not (see Table I below).

TABLE I

| | MFP Stability in BTC Dentifrice With 20% PEG 600 Humectant System and 20% Glycerin Humectant System | | | | | | | | | | | | |
|---|---|---|---|---|---|---|---|---|---|---|---|---|---|
| Humec- | pH | | Soluble F | | | | Ionic F | | | | MFP as F | | |
| tant | I | 9 w* | I | 3 w | 6 w | 9 w* | I | 3 w | 6 w | 9 w* | I | 3 w | 6 w | 9 w* |
| PEG | 8.2 | 10.1 | 980 | 660 | 570 | 520 | 57 | 289 | 439 | 431 | 920 | 370 | 130 | <100 |
| Glyc. | 7.8 | 8.3 | 980 | 870 | 790 | 790 | 26 | 55 | 85 | 106 | 950 | 810 | 700 | 680 |

*w = weeks

This table clearly shows the poor stability of MFP in an all PEG 600 humectant and the very good stability of MFP in an all glycerin formulation.

HPLC (High Pressure Liquid Chromatography) analysis on both a glycerin and a sorbitol BTC dentifrice formulation was performed initially and after nine weeks accelerated aging at 49° C. Two extraction methods for BTC (water and acetone) indicate no decrease in BTC recovery after accelerated aging (see Table II).

TABLE II

| HPLC Analysis On A Glycerin And A Sorbitol BTC Dentifrice Formulation Initially And After Nine Weeks Accelerated Aging (49° C.) | | | | |
|---|---|---|---|---|
| | Initial Analysis | | Analysis After Aging | |
| Humectant | Water Extraction | Acetone Extraction | Water Extraction | Acetone Extraction |
| 20% Glycerin | 0.42 | 0.54 | 0.47 | 0.52 |
| 20% Sorbitol | 0.36 | 0.48 | 0.45 | 0.46 |

The glycerin and/or sorbitol humectant system constitutes about 18–23% by weight of the dentifrice composition.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology, 2nd edition (Vol. 2, pp. 632–635), incorporated herein by reference. Cationic materials which possess antibacterial activity (i.e. are germicides) are used against bacteria and have been used in oral compositions to counter plaque formation caused by bacteria in the oral cavity.

Among the most common of these antibacterial antiplaque quaternary ammonium compounds is benzethonium chloride, also known as Hyamine 1622 or diisobutylphenoxyethoxyethyl dimethyl benzyl ammonium chloride, and cetyl pyridinium chloride. In an oral preparation this material is highly effective in promoting oral hygiene by reducing formation of dental plaque and calculus, which is generally accompanied by a reduction in periodontal diseases. Other cationic antibacterial agents of this type are those mentioned, for instance, in U.S. Pat. Nos. 2,984,639, 3,325,402, 3,431,208 and 3,703,583, and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alky or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5-amino-1,3-bis(2-ethylhexyl)-5-methyl hexa hydro-pyrimidine are typical quaternary ammonium antibacterial agents.

The dentifrice formulation of present invention contains an effective amount of the antiplaque quaternary ammonium compound, preferably about 0.1–1% by weight of the composition.

The ability of quaternary ammonium compounds to inhibit the formation of dental plaque is well known. However, they are deactivated by the anionic surfactants such as sodium lauryl sulfate conventionally used in dentifrice formulations. The substitution of nonionic surfactants for the anionic surfactants eliminates the deactivation problem but results in products with poor foaming. However, the incorporation of betaine surfactants into antiplaque dental formulations based on quaternary active ingredients unexpectedly improves the foaming of these formulations without deactivating the quaternary antibacterial agents.

The betaine component of present dentifrice composition has the general formula:

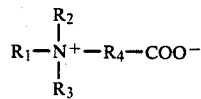

wherein $R_1$ is an alkyl group having 10 to about 20 carbon atoms, preferably 12 to 16 carbon atoms or the amido radical;

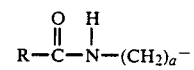

wherein R is an alkyl group having about 10 to 20 carbon atoms and a is the integer 1 to 3; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl betaine or 2-(N-decyl-N,N-dimethylammonio) acetate, coco betaine or 2-(N-coco-N,N-dimethylammonio) acetate, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like.

The betaines, which are zwitterionic materials, function as a foaming agent in the quaternary-containing dentifrice compositions. They act cationically over a wide pH range, but do not deactivate the quaternary antimicrobial activity.

In addition to the non-interference exhibited by the betaines with the quaternary activity, laboratory foam tests have shown that formulations containing both the quaternary ammonium compound (quat) and the betaine, foam 2–3 times better than the nonionic/quat formulations.

The zwitterionic betaines are completely compatible with the quaternary antimicrobial antiplaque agents, and impart detersive and improved foaming properties to the quaternary-containing dentifrice composition without deactivating the antimicrobial properties thereof. The amount of betaine effective in the production of improved foaming may be varied from about 3–5% by weight of the total formulation.

Cosmetic problems of stability is incurred with all zwitterionic-containing dentifrices, such as crimp leakage of flavor. The flavor oozes and is not solubilized in the zwitterionic surfactant. However, stability evaluations of present novel antiplaque dentifrices containing glycerin and/or sorbitol humectant indicate satisfactory flavor stability for nine weeks aging at 49° C. The flavor ingredient which is an essential ingredient in a dentifrice constitutes about 0.5–2% by weight. Any suitable flavor may be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate.

A sweetening material may also be employed as a complement to the flavoring material. Suitable sweetening agents are water soluble and include sucrose, lactose, maltose, sorbitol, sodium cyclamate, and saccharin, in an amount of 0.01–0.5% by weight.

Another essential ingredient in present dentifrice is a gelling agent which is a nonionic gum, in an amount of about 0.8–1.5% by weight. It has been found that large organic anionic molecules such as carboxymethylcellulose have the potential to deactivate the quaternary antibacterial activity. Accordingly, hydroxyethylcellulose, which is a nonionic small organic molecule, effects a stable pituitous gel in the betainequat system of present invention, and is the preferred gelling agent. Other nonionic gelling agents may be used such as hydroxymethylcellulose, and the like.

The fluoride-providing compounds, which are preferably additional ingredients in present dentifrice, are characterized by their ability to release fluoride ions in water and by substantial freedom from reaction with other compounds of the dentifrice. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and difluorophosphate, and fluorinated sodium calcium pyrophosphate. Alkali metal and tin fluorides, such as sodium and stannous fluorides, sodium monofluorophosphate and mixtures thereof, are preferred.

The amount of the fluoride-providing compound is dependent to some extent, upon the type of compound, its solubility, and the dentifrice, but it must be a non-toxic amount. In a solid oral preparation, such as a toothpaste or dental cream, an amount of such compound which releases a maximum of 1% by weight of the preparation is considered satisfactory. Any suitable minimum amount of such compound may be used, but it is preferable to employ sufficient compound to release from 0.005% to 1%, and preferably about 0.1% of fluoride ion. Typically, in the cases of alkali metal fluorides and stannous fluoride, this component is present in an amount up to 2% by weight, based on the weight of the preparation. In the case of sodium monofluorophosphate, the compound may be present in an amount up to 7.6% by weight, more typically 0.76%.

The dentifrice prepared in accordance with this invention, contains conventional water-insoluble polishing materials or dental abrasives, in amounts from about 35-65% by weight of the total formulation. Suitable examples of dental abrasives or polishing materials include sodium metaphosphate, potassium metaphosphate, tricalcium phosphate, dihydrated calcium phosphate, anhydrous discalcium phosphate, calcium pyrophosphate, magnesium orthophosphate, trimagnesium phosphate, calcium carbonate, zirconium silicates, silica, bentonite, and mixtures thereof. The preferred abrasives are alumina-containing abrasives such as calcined alumina and hydrated alumina and mixtures thereof. The abrasive is added to the water gel phase or to the single gel after combining the oil gel and water gel phases.

The dentifrice of this invention may also contain conventional additional ingredients such as coloring or whitening agents, preservatives and ammoniated materials such as monoammonium glycyrrhizinate. These additional ingredients may each be added to the dentifrice in minimal amounts of up to 5% by weight, and preferably up to 1%, provided they do not interfere with the foaming, antiplaque and stability properties of the finished product. The oil phase typically constitutes about 3.6-8% by weight of the dentifrice.

In the practice of this invention to promote oral hygiene, the dentifrice according to this invention is applied regularly to dental enamel by brushing the teeth for 30-90 seconds at least once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated.

EXAMPLE 1

Glycerin Humectant Anti-Plaque Dentifrice

| Ingredients | % |
| --- | --- |
| Water (Deionized) | 19.34 |
| Sodium Saccharin | 0.30 |
| Sodium Monofluorophosphate | 0.76 |
| Hydroxyethylcellulose | 1.10 |
| Glycerin | 20.00 |
| Benzethonium Chloride | 0.50 |
| Flavor | 1.00 |
| Cocamidopropyl Betaine | 5.00 |
| Calcined Alumina | 10.00 |
| Hydrated Alumina | 42.00 |

The benzethonium chloride is dispersed in the flavor and this dispersion is mixed into the betaine to form an oil gel. The sodium saccharin and sodium monofluorophosphate (MFP) are dissolved in the water. Hydroxyethylcellulose is dispersed in the glycerin, and this mixture is added to the water-saccharin-MFP solution with stirring to form a water gel. The oil and water gels are mixed to form a stable parent gel. The calcined alumina and hydrated alumina are admixed with the parent gel to produce the finished dentifrice which is effective against plaque related bacteria while possessing excellent chemical and cosmetic stability as well as having sufficient foaming characteristics. This dentifrice is prepared at room temperature.

EXAMPLE 2

Example 1 is repeated except that 20% sorbitol is substituted for the 20% glycerin. The resultant product is equally effective against plaque related bacteria and also possess excellent chemical and cosmetic stability and sufficient foaming properties.

MFP stability studies indicate that both the new glycerin and sorbitol dentifrices have an excellent MFP stability profile. Example 1 (20% glycerin) had an initial total soluble fluoride value of 900 ppm and an MFP and F value of 950 ppm. Example 2 (20% sorbitol) had an initial total soluble fluoride value and an MFP as F value of 1,020 ppm and 980 ppm respectively (See Table III).

TABLE III

MFP Stability Profile of a New All Glycerin BTC Dentifrice and a New All Sorbitol BTC Dentifrice
(Nine Weeks (w) Aging at 49° C.)

| | | pH | | Soluble F | | Ionic F | | MFP as F | |
| --- | --- | --- | --- | --- | --- | --- | --- | --- | --- |
| Ex. | Humectant | I | 9 w | I | 9 w | I | 9 w | I | 9 w |
| 1 | All Glycerin | 7.8 | 8.0 | 990 | 820 | 43 | 94 | 950 | 730 |
| 2 | All Sorbitol | 7.6 | 7.7 | 1020 | 960 | 43 | 45 | 980 | 910 |

The pH profiles of both formulations showed only a slight increase after nine weeks aging at 49° C. After accelerated aging, values for total soluble fluoride and MFP as F were 820 ppm and 730 ppm respectively for Example 1 and 960 ppm and 910 ppm respectively for Example 2.

Variations in the above formulations may be made. For example, other betaines such as lauramidopropyl betaine, cocobetaine and the like may be substituted for the cocoamidopropyl betaine in the examples. Similarly, other abrasives may be substituted for the specific abrasives in the examples. Likewise, other fluoride-containing compounds such as sodium fluoride, potassium fluoride, etc. may be substituted for the sodium monofluorophosphate in the specific examples. Likewise, cetyl pyridinium chloride or other quaternary ammonium antiplaque agents may be substituted for the benzethonium chloride. Also, sodium cyclamate may replace sodium saccharin.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A chemically and physically stable antiplaque dentifrice comprising an antiplaque quaternary ammonium compound, a betaine surfactant, a flavor, a humectant system of glycerin and/or sorbitol, a nonionic gelling agent, and a water insoluble dental abrasive, prepared by the process which comprises the preparation of two separate gel phases, an oil gel phase consisting essentially of the quaternary ammonium compound, the betaine and flavor; and a water gel phase consisting essentially of water, humectant and nonionic gelling agent; combining said two gel phases into a single parent gel phase; and adding a water-insoluble dental abrasive to said combined gel phase, or adding said abrasive to the water gel phase prior to combining with the oil gel phase.

2. The dentifrice according to claim 1, wherein the flavor constitutes about 0.5–2% by weight.

3. The dentifrice in accordance with claim 1, wherein a water-soluble sweetening material and/or a fluorine-containing compound are dissolved in the formula amount of water prior to the addition of the water to the humectant and gelling agent in the formation of the water gel phase.

4. The dentifrice in accordance with claim 3, wherein said sweetening material is sodium saccharin and said fluorine-containing compound is sodium monofluorophosphate.

5. The dentifrice according to claim 4 wherein sodium saccharin constitutes about 0.01–0.5% by weight.

6. The dentifrice according to claim 1, wherein the betaine content constitutes about 3–5% by weight of the formulation.

7. The dentifrice according to claim 6, wherein the betaine is cocoamidopropyl betaine.

8. The dentifrice according to claim 6, wherein the nonionic gelling agent is hydroxyethylcellulose in amounts of about 0.8–1.5% by weight.

9. The dentifrice according to claim 8, wherein the humectant system of glycerin and/or sorbitol constitutes about 18–23% by weight of the composition.

10. The dentifrice according to claim 1, wherein said dental abrasive constitutes about 35–65% by weight of the composition.

11. The dentifrice according to claim 10, wherein the dental abrasive is an alumina-containing abrasive.

12. The dentifrice according to claim 11, wherein the antiplaque quaternary ammonium compound is benzethonium chloride in an amount of about 0.1–1% by weight.

13. The dentifrice according to claim 11, wherein the abrasive is a mixture of hydrated alumina and calcined alumina.

* * * * *